United States Patent
Flodin (12)

(10) Patent No.: US 6,210,441 B1
(45) Date of Patent: Apr. 3, 2001

(54) LINEAR BLOCK POLYMER COMPRISING UREA AND URETHANE GROUPS, METHOD FOR THE PRODUCTION OF LINEAR BLOCK POLYMERS AND USE OF THE BLOCK POLYMERS AS IMPLANTS

(75) Inventor: Per Flodin, Hovas (SE)

(73) Assignee: Artimplant Development Artdev AB (SE)

( * ) Notice: Subject to any disclaimer, the term of this patent is extended or adjusted under 35 U.S.C. 154(b) by 0 days.

(21) Appl. No.: 09/091,073
(22) PCT Filed: Nov. 25, 1996
(86) PCT No.: PCT/SE96/01530
§ 371 Date: Oct. 5, 1998
§ 102(e) Date: Oct. 5, 1998
(87) PCT Pub. No.: WO97/22643
PCT Pub. Date: Jun. 26, 1997

(30) Foreign Application Priority Data

Dec. 15, 1995 (SE) .................................................. 9504495

(51) Int. Cl.$^7$ ...................................................... A61F 2/08
(52) U.S. Cl. ..................................... 623/13.18; 623/13.13
(58) Field of Search ..................................... 623/1.49, 1.5, 623/1.51, 1.52, 1.53, 1.54, 13, 13.13, 13.18

(56) References Cited

U.S. PATENT DOCUMENTS 3,895,043 * 7/1975 Wagner et al. .................... 260/448.8
4,549,010 * 10/1985 Sparer et al. ........................ 528/361

FOREIGN PATENT DOCUMENTS

89/05319 * 6/1989 (WO) .
92/00338 * 1/1992 (WO) .
92/04390 * 3/1992 (WO) .

OTHER PUBLICATIONS

Publication Under the PCT, WO 92/00338; Pub. Jan. 9, 1992, Int'l Appl #PCT/AU91/00270; Priority date Jun. 26, 1990.

Publication Under the PCT, WO 92/04390; Pub. Mar. 19, 1992, Int'l Appl #PCT/US91/06621; Priority date Sep. 12, 1991.

\* cited by examiner

Primary Examiner—Michael J. Milano
Assistant Examiner—Hieu Phan
(74) Attorney, Agent, or Firm—John S. Munday

(57) ABSTRACT

Linear block polymer having a molecular weight of at least $10^4$ Dalton, comprising urea and urethane groups and ester groups at such a distance from each other that after hydrolysis of these ester groups fragments are created which are so small that they are biologically degradable and can be excreted from a human body and further including an end group selected from primary $NH_2$ and OH groups, which can be substituted by a monoamine. The polymers are intended to be used as implants.

17 Claims, No Drawings

LINEAR BLOCK POLYMER COMPRISING UREA AND URETHANE GROUPS, METHOD FOR THE PRODUCTION OF LINEAR BLOCK POLYMERS AND USE OF THE BLOCK POLYMERS AS IMPLANTS

FIELD OF THE INVENTION

The present invention relates to a linear block polymer which comprises urea and urethane groups and which has a high molecular weight and which is suited as an implant in living beings such as humans and animals. The invention also comprises a method for the production of the block polymer in question and use thereof as an implant, for example, an implant in the form of ligaments.

PRIOR ART

When injuries arise on the body of a human or an animal or as a result of some disease, a damaged organ must often be replaced temporarily or permanently by some kind of implant. A condition for such an implant to be able to be used is that, firstly, it has such properties, for example strength, that it can replace the functions of the damaged organ and, secondly, that it is biocompatible, i.e. that the body is not poisoned or in some other way damaged by the implant. Different materials, such as pure titanium and some kinds of plastic materials have been shown to have these properties and are already used to a great extent. Other materials are also known in this connection.

The metallic implants, such as titanium and some types of steel are characterized by their great strength and they are therefore used, for example, as tooth implants or for repairing bone fractures, etc. Surgically inserted reservoir containers for medicines which are to be dosed in small amounts during an extended period of time are preferably made of titanium. Different forms of pipes which can replace blood veins or drain out some body liquid are used and these are usually made of thermoplastic materials. They may be used both temporarily and permanently.

Technical Problem

Some implants, such as implants for replacing or supporting a ligament, must have a certain tension strength and have an adapted stretchability. In addition, it is necessary for such an implant that it is also biocompatible and it is also desirable that the implant can promote the growth of the damaged natural ligament at the same time as the implant in many cases should be biologically degradable so that it slowly disappears and the rebuilt ligament resumes its function again.

Solution

According to the present invention, the above problems have been solved and an implant has been created using a new linear block polymer having a molecular weight of at least $10^4$ Dalton, preferably at least $10^5$ Dalton, comprising urea and urethane groups and ester groups at such a distance from each other that after hydrolysis of these ester groups fragments are created which are so small that they can be excreted from a human body and further comprising primary $NH_2$ and/or OH end groups, which can be substituted by for example monoamines, such as butylamine or ethylamine.

According to the invention, the linear block polymer should have at least as many or more urea groups as urethane groups.

The linear block polymer according to the present invention can, in the chain, also contain such groups as polytetramethylene oxide, polyethylene oxide, polycaprolactone, polyethylene glycol adipate, tolylene, diphenyl methane, hexamethylene, tetramethylene, naphthylene, glycerine monoallyl ether, trimethylol propane monoallyl ether, glycerine monoglycidyl ether, dimethylol propionic acid methyl ester, dimethylol propionic acid bromobutyl ester, esters of monocarboxymethyl ethers of glycerine and trimethylol propane and other additional groups which modify the properties of the block polymer.

The invention also includes a method for the production of linear block polymers and it is characterized in that a prepolymer having two isocyanate end groups per molecule is chain extended with an aliphatic or aromatic diamine having a mol ratio of $NH_2/NCO$ of 0.95–1.05, preferably 0.98–1.02.

According to the invention, the prepolymer is suitably produced by providing a diol with two isocyanate end groups per molecule. The prepolymer may be a mixture of prepolymers having different composition.

According to the invention, it is suitable that the diol consists of a polyester diol, for example, polydiethylene glycol adipate diol, polycapro-lactone diol or polyethylene glycol adipate diol, or a polyether diol such as polytetramethylene oxide diol, polyethylene oxide diol or a monodiol such as glycerine monoallyl ether, trimethylol propane monoallyl ether, glycerine monoglycidyl ether, dimethylol propionic acid methyl ester, dimethylol propionic acid bromobutyl ester, esters of monocarboxymethyl ethers of glycerine, trimethylol propane, and others and the isocyanate-supplying compound is suitably 4, 4'-diphenyl methane diisocyanate, tolylene diisocyanate, hexamethylene diisocyanate, tetramethylene diisocyanate, naphthylene diisocyanate and others. The diol may also consist of mixtures of diols.

According to the invention, it is suitable that the diamine consists of primary diamines, preferably ethylene diamine or 1.3-diaminopropane or hydrolysable diamines, for example, 1.3-propane diol-bis-p-aminobenzoate or ethylene glycol-bis-diamino acetate.

The molecular weight and its distribution may, according to the invention, be controlled by the stoichiometric relationship but primarily by addition of small amounts of monoamine, for example butyl amine or ethanol amine.

The method according to the invention also includes that built-in groups in the chain are modified by a reaction with physiologically active substances. Those groups which, according to the invention, are modified are suitably glycerine monoallyl ether, trimethylol propane monoallyl ether, glycerine monoglycidyl ether, dimethylol propionic acid methyl ester, and dimethylol propionic acid bromobutyl ester.

The linear block polymer according to the invention is suitable as material in implants in humans and animals.

When the block polymer is used as an implant this is suitably an implant for ligaments, tendons, skin or cartilage.

According to the invention, it is suitable that when the polymer is used as an implant it has the form of fibres or threads which have been knitted or woven.

According to the invention, it is suitable that the block polymer, by means of its $NH_2$ or OH end groups, is used for covalent binding of growth-promoting groups. The OH groups can be obtained by, for example, using ethanol amine as a chain stopper.

DETAILED DESCRIPTION

Block polymers or block copolymers are defined as copolymers in which participating monomers are present as sequences or blocks of different lengths which are linearly united to each other to molecules having a high molecule weight (>$10^4$ Dalton). The latter is important for the mechanical properties and necessary for making fibres and films.

An advantage of block polymers is that properties which are characteristic for several homopolymers can be built in in one and the same molecule. In this way, incompatible polymers can be brought to cooperate in a material and apparently non-compatible properties can be combined. Thus, reactive side groups can be introduced. Further, hydrolysable blocks may, for example, be introduced which, after hydrolysis, give fragments of polymers which are sufficiently small to be secreted from the body.

A common way to describe block polymers is as follows. The monomer A forms the block A-A-A-A-A . . . , called polyA or pA and the monomer B forms the block B-B-B-B . . . , polyB or pB. They are united to -A-A-A-A-B-B-B- or pA-pB in the production process. Typical block polymer types are diblock, triblock and multiblock polymers. In the present invention, the multiblock type is the one mostly used. It is written pA-pB-pA-pB-pA-pB . . . in which the block types alternate. By partially exchanging the block types, variants can be produced which give further properties to the polymer. The invention relates to production of such variants in which the third component (and possibly a fourth) randomly replaces one of the blocks, for example pB.

The invention uses isocyanate chemistry to synthesise the block polymers, which will be of the type polyurethane urea groups. Both form hydrogen bonds between the molecules, which gives the cohesive forces which are needed to keep the molecules together in a material. Especially strong intermolecular forces are obtained by the urea groups especially when several groups have the possibility to cooperate. For this reason, the cohesive forces grow strongly when the amount of urea blocks increases.

The polyurea blocks will henceforth be denoted by pA and the others by pB, pC, etc. They are usually formed at the chain extension when the isocyanate group-terminated prepolymers are coupled to diamines according to the formula

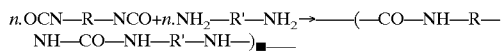

in which OCN—R—NCO is a urethane diisocyanate formed of a diol and a diisocyanate according to the formula

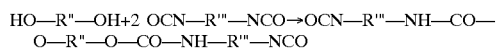

in which R is pB, pC, etc. blocks as above. In the reaction the stoichiometry is very important. Thus, n must have so great a value that it corresponds to molecular weights of at least $10^4$, preferably $10^5$ or more, if satisfactory mechanical properties are to be obtained. To reach such high values the molar ratios of —$NH_2$/—NCO=0.95–1.05 are used. The excess of —$NH_2$ gives end groups of a primary amine character which can be used to covalently attach biologically active groups to the polymer molecules. If ethanol amine is used as a chain stopper, OH end groups are obtained which also can be used for coupling of active agents, for example growth factors to the polymer. Excess of isocyanate groups gives end groups which can react further according to known isocyanate reactions.

If better mechanical properties are desired by means of more and/or longer urea blocks, this can be obtained in, for instance, the following two ways:

1. During the chain extension reaction further diisocyanate and a corresponding amount of diamine are added. Care must be taken when increasing the average length of the urea blocks since formation of unmeltable gel can be obtained even on a moderate increase of the length.

2. An isocyanate group terminated prepolymer containing urea groups is added during the chain extension reaction. The prepolymer must be dissolved in the reaction mixture when the reaction of the chain extension is started.

As a chain extender, primary diamines are preferably used, which may be aliphatic or aromatic. Primary aliphatic diamines give very high reaction velocity, which can cause inhomogeneous reactions and hence an inhomogeneous product. The reaction velocity can be modified by using aromatic amines the structure of which is very significant for the reactivity or by adding some agent which cooperates with the amine and/or isocyanate groups such as acetone, oximes, or the like. Considerable possibilities to control the activity are consequently present.

The chain extension may also occur in solvents which dissolve the starting products but not the polymer. The product precipitates, for example, as a powder and it can then be obtained by filtering.

The polyurea blocks pA are often called "hard" since they are responsible for the cohesion of the materials, which is a function of the content and the length thereof. Correspondingly, the pB are often called "soft" blocks since they give the materials the stretchability and elasticity. In known materials produced on a large scale they consist of polytetramethylene oxide diol. Other examples are polyethylene oxide diol, polycaprolactone diol, polyethylene glycol adipate diol, etc. All of them have hydroxyl end groups and are transformed to prepolymers by reaction with diisocyanates according to the formula:

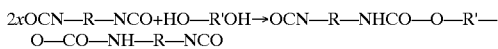

In the formula two mol diisocyanate per mol diol have been stated. This gives the shortest possible prepolymer. If longer prepolymers are wanted, less than two mol diisocyanate per mol diol is used according to known relations from polymer chemistry. At the reaction urethane groups are formed. It can be carried out at an elevated temperature (60–80° C.) or at lower temperatures in the presence of a catalyst. Too high temperatures (>90° C.) should be avoided to minimise non-desired side reactions, for example, di- or trimerising of the isocyanate.

The isocyanates used in the invention must be bifunctional so that the formed polymers are linear and can form fibres and films. Preferably, the content of bifunctional molecules should be greater than 99%. If the impurities consist of agents that do not take part in the reaction, then a somewhat lower content of isocyanate can be tolerated. If monoisocyanates are present they will bring about a termination of the molecules. If isocyanates having three or more isocyanate groups are present, branched molecules or cross-bound polymers are formed which cannot be spun to fibres or form films. Among useable isocyanates, tolylene diisocyanate (TDI), diphenylmethane-4,4'-diisocyanate (MDI), hexamethylene diisocyanate (HDI), tetramethylene diisocyanate, naphthylene diisocyanate, and others may be mentioned.

In a corresponding way to that described above, prepolymers for other functional blocks (pC,pD, etc.) can be produced. In principal, every diol which does not contain other groups than hydroxyl groups which react with isocyanate can be used. Examples thereof are glycerine monoallyl ether, trimethylol propane monoallyl ether, glycerine monoglycidyl ether, dimethylol propionic acid methyl ester, dimethylol propionic acid bromobutyl ester, esters of monocarboxymethyl ethers of glycerine, trimethylol propane and many others. These either have, or they can be converted by known methods to, epoxy groups which in their turn after the chain extension can be reacted in a number of ways to facilitate binding to biologically active groups such as growth-promoting peptides.

The chain extension reaction is suitably carried out in a solution to decrease the speed of reaction, viscosity and tendency of gel formation. Dimethyl formamide, dimethylacetamide, dimethylsulphoxide or some similar polar solvent may be used as solvents. The solution obtained can be used as a dope for fibre spinning directly or after modification.

Alternatively, as mentioned above, the chain extension may be carried out in an agent which dissolves the starting products but in which the polymer is insoluble. In that case the product is dissolved in a solvent before spinning, which is performed in the same way as above.

The spinning can be done either as dry spinning or as wet spinning according to known methods. The latter method includes that the dope is inserted via the spinning nozzle into water. In connection with the coagulation, the fibre bunch may be stretched to the desired stretching degree, whereupon the thread is wound up while being simultaneously twisted.

In an analogous way, film can be produced by moulding on rollers, coagulating, stretching and winding up. The stretched film can thereafter be cut into fibre-like strips.

EXAMPLE 1

Polydiethylene glycol adipate diol with a molecular weight of 560 was dried in vacuum for 16 hours. In a three-necked flask with thermometer and stirrer 90.78 g of crystalline 4,4'-diphenyl methane diisocyanate (MDI) was melted, whereupon 99.86 g polydiethylene glycol adipate diol having a molecular weight of 560 was added dropwise during heating. The reaction temperature was maintained by cooling between 80 and 90° C. The reaction was complete after four hours. The content of isocyanate was determined titrimetrically and was 1.22.

The prepolymer obtained (22.81 g) was dissolved in dimethyl formamide to a concentration of 20%. It was chain extended using a slight excess of ethylene diamine (1.05 g) at room temperature under most possible effective stirring. The reaction was complete a few minutes after the addition was completed.

Film was produced by spreading out the solution on a glass plate and evaporating the solvent in a desiccator cabinet. The film obtained was flexible and mechanically strong even in a humid atmosphere.

The solution was wet-spun by extrusion through a spinning nozzle having 50 orifices with a diameter of 80 μm in a water bath. The fibre bunch obtained (the thread) was stretched 5 times in a subsequent water bath and wound up on a bobbin. After rinsing in water for two days and drying, the strength was measured in a tensioning measuring apparatus to 1.6 N and the break elongation was 70%. Bands were woven from the fibres and surgically inserted into rabbit knees.

EXAMPLE 2

102.2 g of a polycaprolactone diol having a molecular weight of 2000 was added dropwise to 17.19 g hexamethylene diisocyanate at a temperature of 80–90° C. during three hours. 42.1 g of the product, which had an isocyanate number of 0.78, was dissolved to a 25% solution in dimethyl formamide. The solution was cooled to 0° C. and reacted under vigorous stirring with 0.96 g ethylene diamine and 0.039 g ethanol amine. The reaction was practically instantaneous.

After dilution with dimethyl formamide to a concentration of 15% and addition of 12 g LiCl, a clear solution was obtained which was wet-spun in water through a nozzle having 50 orifices with a diameter of 80 μm, stretched six times and wound up on a bobbin. After rinsing in water, the thread had a break strength of 1.18 N and a break elongation of 80%.

EXAMPLE 3

118 g dry polycaprolactone having a molecular weight of 530 was added dropwise to 11.32 g diphenyl methane diisocyanate (MDI) while the temperature was maintained at 70–80° C. during 2 hours. From the prepolymer formed (isocyanate number 1.98) 16.13 g was dissolved in dimethylsulphoxide (DMSO) to a 15% solution and 0.95 g ethylene diamine and 0.04 g ethanol amine dissolved in DMSO was added at 20° C. The solution, which rapidly became highly viscose, was stirred for one hour, whereupon it was wet-spun in the same way as in Example 1. The thread obtained had a break strength of 1.1 N and the break elongation was 22%. The thread had the text number 7.

EXAMPLE 4

98.78 g dry polycaprolactone with a molecular weight of 1250 was added dropwise to 39.51 g MDI during 3 hours at a maintained temperature of 70–80° C. From the prepolymer, which had the isocyanate number 1.2, 30.48 g was dissolved in acetone and 1.13 g ethylene diamine was added under vigorous stirring at 20° C. A white pulverulent product was formed which could be dissolved in DMF+LiCl and wet-spun to a thread. The break tension was 2.18 N and the break elongation 175%.

EXAMPLE 5

A prepolymer was produced from 47.58 g poly(1.4-butane diol adipate) with a molecular weight of 600 and 90.2 g MDI by adding the dry polyester dropwise into the melted isocyanate for 2 hours at a maintained temperature of 70–80° C. The isocyanate number for the finished prepolymer was 1.61.

29.78 g was taken from the prepolymer and dissolved to a 30% solution in dimethylsulphoxide (DMSO). 7.72 g 1,3-propane diol-bis-p-aminobenzoate was added and chain extension was carried out at 100° C. during 22 hours while stirring. A clear solution was obtained which could be spun to fibres according to the method given in Example 1. The thread was stretched 4 times. The break tension was 0.8 N and the break elongation 200%.

EXAMPLE 6

From a prepolymer of diethylene glycole adipat having a moleculare weight of 375 and MDI were 17.02 mixed with 6.12 g of a second prepolymer made by 3-allyloxy-1-2-propan diol and MDI (molar ratio 1–2) by solving in DMSO. The isocyonite number was measured to 2.52 M-mol/g. Chain extending was made at room temperature with 2.17 g 1–2 diamino propane containing 0.07 g ethanole amine solved in a mixture of 3.5 g acetone and 30 g DMSO. A highly viscous solution was obtained which had to be diluted with 15% solids to make spinning possible. The solution was wet spun through a nozzle having 60 holes (diameter 80 mm) down into water at a temperature of 80° C.). The thread was stetched 6 times in water at 80° C. The thread obtained had a titer of 3 Tex and a specific break tension of 0.17 N/Tex.

EXAMPLE 7

From the prepolymer of example 3 22 g was dewatered in vacuuo at 100° C. 6.5 g 1,3-propandiol-bis-p-aminobenzoate was melted in a heating chamber at 140° C. and mixed with the warm prepolymer. The mixture was poured into a cylindrical form which was maintained in a heating chamber at 100° C. during 18 hours. The formed cylindrical body was yellow and had a hardness of 72 on the Shore D-scale.

EXAMPLE 8

A prepolymer was produced from polykaprolactone having a molecular weight of 530 and dicyklo hexyl metan diisocyanat (H12 MDI) in a moler ratio of 1–2. From this prepolymer 27 g was solved in 122.4 g DMF and 1.9 g 1.3-diaminopropane solved in 41 g DMF was added at room temperature. After the reaction was finished the solution was wet spun as in example 1 and stretched 5 times. The specific break tension was 0.20 N/Tex.

EXAMPLE 9

The polymer in example 6 was reacted with an eccess (compared to the allylic dubble bonds in the polymer) of merkapto ethanol with azo-bis-isobutyronitril as a catalyst. Hereby an aduct was formed having protruding hydroxyle groups from the polymer chain. After precipitation in water and washing with water and DMSO the polymer was solved in the DMSO and reacted with the peptid glycyl-histidyl-lysin (GHK) under influence of dicyklo hexyl karbodiimid. After the reaction was finished film was molded which was washed with destined water, contacted with a solution of copper (II) sulfate in water and washed in destined water until copper iones could not be shown in the water. Tissue growth of condrocytes on a film produced in this way showed a strongly improved growth rate compared to a non-treated control film.

The polymers according to the invention can be fragmented in a biological environment and they can be bound to growth-promoting groups. They are film and fibre forming and they have mechanical properties sufficient for the production of woven or twisted bands useful as ligament prostheses.

As stated above, the polymers according to the invention can be used as temporary implants. These are connected in a suitable surgical way to the damaged body part, for example the ligament, whereupon the damaged body part can grow and heal with the protection and assistance of the implant. After the healing is complete, this can be removed or it can be fragmented during the healing and be secreted from the body.

The invention is not limited to the above-stated embodiments but can be varied in different ways within the scope of the claims.

What is claimed is:

1. Linear block polymer having a molecular weight of at least $10^4$ Dalton, comprising urea and urethane groups and ester groups at such a distance from each other that after hydrolysis of these ester groups fragments are created which are so small that they are biologically degradable and can be excreted from a human body and further including an end group selected from primary $NH_2$ and OH groups, which can be substituted by a monoamine.

2. Linear block polymer according to claim 1, wherein the urea groups are equal with or greater in number than the urethane groups.

3. Linear block polymer according to any of claim 1, whereby in said linear block it also contains groups derived from polytetramethylene oxide, polyethylene oxide, polycaprolactone, polyethylene glycol adipate, toluylene, diphenyl methane, hexamethylene, tetramethylene, naphthylene, glycerine monoallyl ether, trimethylol propane monoallyl ether, glycerine monoglycidyl ether, dimethylol propionic acid methyl ester, dimethylol propionic acid bromobutyl ester, esters of monocarboxymethyl ethers of glycerine and trimethylol propane and other additional groups which modify the properties of the block polymer.

4. Method for the production of linear block polymers according to any of claim 1, wherein a prepolymer having two isocyanate end groups per molecule is chain extended with an aliphatic or an aromatic diamine having a mol ratio $NH_2/NCO$ of 0.95–1.05.

5. Method according to claim 4, wherein the prepolymer is produced from a diol with two isocyanate groups per molecule.

6. Method according to claim 5, wherein the diol is a polyester diol, selected from the group consisting of, polycapro-lactone diol polydiethylene glycol adipate diol or polytetramethylene oxide diol, polyethylene oxide diol, polyethylene glycol adipate diol, glycerine monoallyl ether, trimethylol propane monoallyl ether, glycerine monoglycidyl ether, dimethylol propionic acid methyl ester, dimethylol propionic acid bromobutyl ester, esters of monocarboxymethyl ethers of glycerine and trimethylol propane, and the isocyanate-supplying compound of 4,4'-diphenyl methane diisocyanate, toluylene diisocyanate, hexamethylene diisocyanate, tetramethylene diisocyanate, and naphthylene diisocyanate.

7. Method according to any of claim 6, wherein the diamine comprises ethylene diamine or hydrolysable diamines, selected from the group consisting of DMAB and ethylene glycol bis glycine ester diamine.

8. Method according to any of claim 1, wherein the molecular weight and its distribution are controlled by stoichiometry or by addition of small amounts of monoamine, selected from the group consisting of butyl amine and ethanol amine.

9. Method according to any of claim 1, wherein said linear block includes groups that are modified by reaction with physiologically active substances.

10. Method according to claim 9, wherein the groups consist of glycerine monoallyl ether, trimethylol propane monoallyl ether, glycerine monoallyl ether, dimethylol propionic acid methyl ester, dimethylol propionic acid bromobutyl ester.

11. Use of the linear block polymer according to any of claim 1 as material in implants in humans and animals.

12. Use according to claim 11, wherein the block polymer is part of or wholly an implant for ligaments, tendons, skin or cartilage.

13. Use according to any of claim 11, wherein the block polymer is present in the form of fibres or threads and is knitted or woven.

14. Use according to any of claim 11, wherein the $NH_2$ or OH end groups of the block polymer are use for covalent binding of growth-promoting groups.

15. The method of claim 6, wherein the diamine comprises a primary diamine.

16. The linear block polymer of claim 1, wherein said monoamine is selected from the group consisting of butylamine or ethylamine.

17. The linear block polymer of claim 4, wherein said mole ratio ranges from 0.98–1.02.

* * * * *